United States Patent
Hoang et al.

(10) Patent No.: US 9,983,062 B2
(45) Date of Patent: May 29, 2018

(54) PHOTOELECTRIC CONVERSION ELEMENT AND WAVELENGTH SENSOR

(71) Applicant: IMRA JAPAN KABUSHIKI KAISHA, Sapporo-shi, Hokkaido (JP)

(72) Inventors: Vu Chung Hoang, Sapporo (JP); Koki Hayashi, Sapporo (JP); Yasuo Ito, Sapporo (JP)

(73) Assignee: IMRA JAPAN KABUSHIKI KAISHA, Sapporo-shi (JP)

( * ) Notice: Subject to any disclaimer, the term of this patent is extended or adjusted under 35 U.S.C. 154(b) by 0 days. days.

(21) Appl. No.: 15/508,811

(22) PCT Filed: Jul. 15, 2016

(86) PCT No.: PCT/JP2016/071080
§ 371 (c)(1),
(2) Date: Mar. 3, 2017

(87) PCT Pub. No.: WO2017/014205
PCT Pub. Date: Jan. 26, 2017

(65) Prior Publication Data
US 2017/0276547 A1  Sep. 28, 2017

(30) Foreign Application Priority Data

Jul. 21, 2015 (JP) .................. 2015-144076
Feb. 5, 2016 (JP) .................. 2016-020993

(51) Int. Cl.
*G01N 21/25* (2006.01)
*G01J 3/51* (2006.01)
(Continued)

(52) U.S. Cl.
CPC ............ *G01J 3/51* (2013.01); *G01J 3/021* (2013.01); *G01J 9/00* (2013.01); *G01N 21/255* (2013.01);
(Continued)

(58) Field of Classification Search
CPC ...... G01J 3/02; G01J 3/51; G01J 9/00; G01N 21/25; H01L 27/14; H01L 31/08
See application file for complete search history.

(56) References Cited

U.S. PATENT DOCUMENTS 8,216,872 B1 * 7/2012 Shieh ............... G02B 5/0242
                                                 438/69
2013/0081692 A1   4/2013 Ihara et al.
2013/0118552 A1   5/2013 Gu et al.

FOREIGN PATENT DOCUMENTS

JP   H09-259943 A   10/1997
JP   2009-070768    4/2009
(Continued)

OTHER PUBLICATIONS

International Search Report issued in International Patent Application No. PCT/JP2016/071080.

*Primary Examiner* — Abdullahi Nur
(74) *Attorney, Agent, or Firm* — Oliff PLC

(57) ABSTRACT

A photoelectric conversion element is realized in which the movement direction of electrons in the element changes according to the wavelength of light to be converted. A photoelectric conversion unit includes an active layer on which light to be converted is incident, an intermediate layer that is arranged on the active layer on a side opposite to the side on which the light to be converted is incident, and a reflection layer that is arranged so as to oppose the active layer with the intermediate layer interposed therebetween. The active layer includes a plasmonic material, which is a material in which plasmon resonance occurs due to a reciprocal action with the light to be converted. The intermediate layer has both a semiconductor property and transparency with respect to the light to be converted. The reflection layer has reflectivity with respect to the light to be converted.

7 Claims, 9 Drawing Sheets

(51) Int. Cl.
*G01J 3/02* (2006.01)
*G01J 9/00* (2006.01)
*H01L 27/146* (2006.01)
*H01L 31/08* (2006.01)
*G01J 3/28* (2006.01)

(52) U.S. Cl.
CPC ............ *H01L 27/146* (2013.01); *H01L 31/08* (2013.01); *G01J 3/2803* (2013.01); *G01N 2021/258* (2013.01)

(56) References Cited

FOREIGN PATENT DOCUMENTS

| JP | 2009-071147 A | 4/2009 |
| JP | 2010-225478 A | 10/2010 |
| WO | 2011/115292 A1 | 9/2011 |

\* cited by examiner

PHOTOELECTRIC CONVERSION ELEMENT AND WAVELENGTH SENSOR

BACKGROUND

Described herein is a photoelectric conversion element and a wavelength sensor.

There is known to be a photoelectric conversion element disclosed in JP 2009-71147A (Patent Document 1). The photoelectric conversion element disclosed in Patent Document 1 is a plasmon resonance photoelectric conversion element that uses plasmon resonance to convert light energy into electrical energy. As disclosed in paragraph 0031 of Patent Document 1, with this photoelectric conversion element, electrons on a metal thin film surface that have been excited due to light absorption caused by plasmon resonance move to a semiconductor thin film, and thereby electrical energy is generated.

Incidentally, as is evident from FIG. 7 of Patent Document 1, the strength of light absorption (absorbance) caused by plasmon resonance is wavelength-dependent, and as a result, the photoelectric conversion efficiency is also wavelength-dependent following a similar trend. However, the wavelength dependence of the photoelectric conversion efficiency is merely a phenomenon in which the degree of efficiency of the energy conversion changes according to the wavelength of the light to be converted, which is light to be subjected to photoelectric conversion, and the movement direction of the electrons in the photoelectric conversion element is basically the same direction regardless of the wavelength of the light to be converted. For this reason, for example, if consideration is given to using the wavelength dependence of an output signal of the photoelectric conversion element, the difference between the output signals for different wavelengths is not necessarily clear. However, no special recognition of this point is made in Patent Document 1.

PRIOR ART DOCUMENTS

Patent Documents

Patent Document 1: JP 2009-71147A (paragraph 0031, FIG. 7)

BRIEF SUMMARY

In view of this, realization of a photoelectric conversion element in which the movement direction of electrons in the element changes according to the wavelength of the light to be converted is desired.

In view of the foregoing problems, a photoelectric conversion element that includes a photoelectric conversion unit and an electrode for connecting the photoelectric conversion unit to an external circuit lies in that the photoelectric conversion unit includes an active layer on which light to be converted, which is light that is to be subjected to photoelectric conversion, is incident, an intermediate layer that is arranged on the active layer on a side opposite to the side on which the light to be converted is incident, and a reflection layer that is arranged so as to oppose the active layer with the intermediate layer interposed therebetween, the active layer includes a plasmonic material, which is a material in which plasmon resonance occurs due to a reciprocal action with the light to be converted, the intermediate layer has both a semiconductor property and transparency with respect to the light to be converted, and the reflection layer has reflectivity with respect to the light to be converted.

According to the above-described configuration, a reflection layer that has reflectivity with respect to the light to be converted is included on the active layer on the side (i.e., the side from which the light to be converted is emitted) opposite to the side on which the light be converted is incident, and the intermediate layer arranged between the active layer and the reflection layer has transparency with respect to the light to be converted. Accordingly, the light to be converted that has passed through the active layer can be caused to be incident on the active layer once again by being reflected by the reflection layer, and the reciprocal action between the light to be converted and the plasmonic material included in the active layer can be strengthened accordingly. In other words, according to the above-described characteristic configuration, in comparison with a case in which the intermediate layer and the reflection layer are not included, the reciprocal action between the light to be converted and the plasmonic material included in the active layer can be strengthened, and as a result, the percentage of the light to be converted that is absorbed in the active layer can be increased. Note that the intermediate layer has a semiconductor property in addition to transparency with respect to the light to be converted, and therefore even if this kind of intermediate layer is included, movement of electrons between the active layer and the reflection layer at the time of generating electrical energy is allowed.

Also, as a result of being able to increase the percentage of the light to be converted that is absorbed in the active layer as described above, it is possible to set the movement directions of electrons between the active layer and the intermediate layer to be mutually opposite in the case where the wavelength of the light to be converted is longer than the specific wavelength and in the case where the wavelength of the light to be converted is shorter than the specific wavelength. Here, the specific wavelength is a wavelength that is shorter than the resonance wavelength for plasmon resonance (hereinafter referred to as "plasmon resonance wavelength"). In other words, one electrical phenomenon among an electrical phenomenon in which the electrons move from the active layer to the intermediate layer and an electrical phenomenon in which the electrons move from the intermediate layer to the active layer can be caused to occur when the wavelength of the light to be converted is longer than the specific wavelength, and the other electrical phenomenon can be caused to occur when the wavelength of the light to be converted is shorter than the specific wavelength.

As described above, with the above-described configuration, it is possible to realize a photoelectric conversion element in which the movement direction of electrons in the element changes according to the wavelength of the light to be converted.

DETAILED DESCRIPTION

Figure 1:
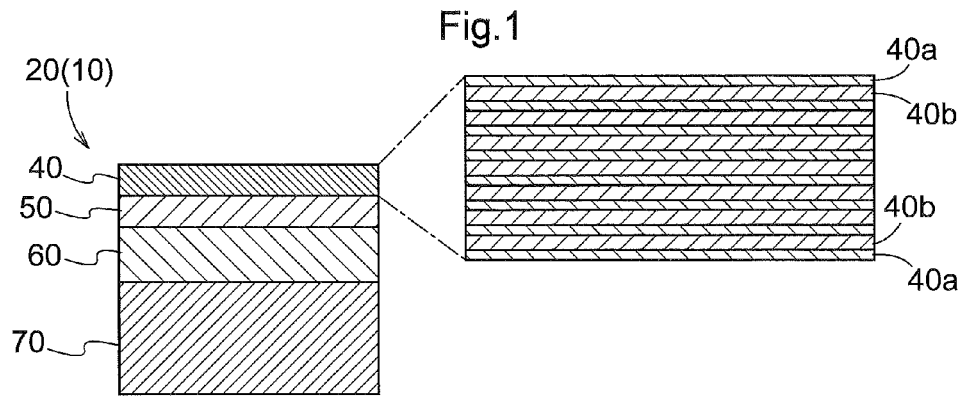
FIG. 1 is a schematic drawing showing an example of a cross-sectional structure of a photoelectric conversion unit according to an embodiment.

Embodiments of a photoelectric conversion element and a wavelength sensor will be described with reference to the drawings. Note that in FIGS. 1 and 4, which are referenced in the following description, the proportion of the thicknesses (widths in the up-down direction in the drawings) of the layers constituting the photoelectric conversion unit (photoelectric conversion element) does not necessarily accurately reflect the actual proportion thereof. Also, the cross-sectional structure (layer configuration) of the photoelectric conversion unit (photoelectric conversion element) is shown simplified in FIGS. 1 and 4. For example, in the present embodiment, a plasmonic layer 40a is a layer including multiple minute particles (nanoparticles), but in FIG. 1, the minute particles are not shown, and both the plasmonic layer 40a and a non-plasmonic layer 40b stacked thereon are shown simplified as uniform layers with homogeneous thicknesses.

1. Configuration of Photoelectric Conversion Element

Figure 4:
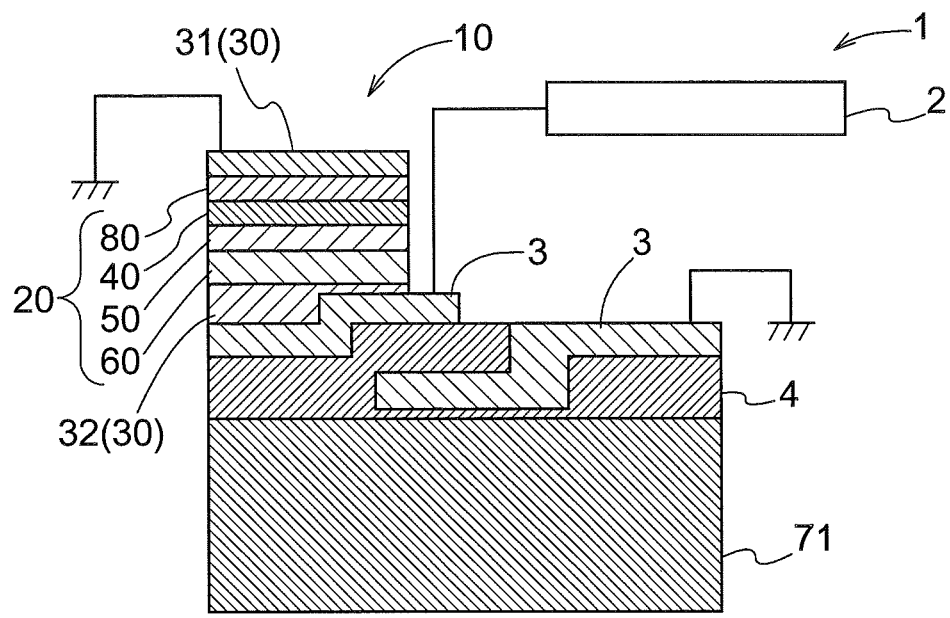
FIG. 4 is a schematic drawing showing an example of a wavelength sensor according to an embodiment.

As shown in FIGS. 1 and 4, a photoelectric conversion element 10 includes a photoelectric conversion unit 20 and electrodes 30. The electrodes 30 are electrodes for connecting the photoelectric conversion unit 20 to an external circuit. Here, the external circuit is an electrical circuit provided outside of the photoelectric conversion unit 20 (outside of the photoelectric conversion element 10). As in the example shown in FIG. 4, if the photoelectric conversion element 10 is to be used in a wavelength sensor 1, the wavelength sensor 1 includes an external circuit that is connected to the photoelectric conversion unit 20 via the electrodes 30. In the example shown in FIG. 4, the wavelength sensor 1 includes the photoelectric conversion element 10 and a wavelength information output unit 2 that is electrically connected to the photoelectric conversion element 10, and the circuit including the wavelength information output unit 2 corresponds to an "external circuit".

The photoelectric conversion element 10 includes the photoelectric conversion unit 20, which converts light energy into electrical energy. As shown in FIG. 1, the photoelectric conversion unit 20 includes an active layer 40, an intermediate layer 50, and a reflection layer 60. The active layer 40 is a layer on which the light to be converted, which is light to be subjected to photoelectric conversion, is incident. The intermediate layer 50 is a layer that is arranged on the active layer 40 on a side (hereinafter referred to as "side from which light to be converted is emitted") that is opposite to the side on which the light to be converted is incident. In the example shown in FIG. 1, the upper side of the drawing is the side on which the light to be converted is incident in the active layer 40, and the lower side in the drawing is the side from which light to be converted is emitted in the active layer 40. The reflection layer 60 is a layer that is arranged so as to oppose the active layer 40 with the intermediate layer 50 interposed therebetween. That is, the intermediate layer 50 and the reflection layer 60 are stacked in the stated order on the active layer 40. In other words, the intermediate layer 50 and the active layer 40 are stacked in the stated order on the reflection layer 60. Hereinafter, the direction in which the intermediate layer 50 and the reflection layer 60 are stacked, which is the direction in which the active layer 40 and the intermediate layer 50 are stacked, that is, the up-down direction in FIG. 1, will be referred to as the "stacking direction". In FIG. 1, a mode in which the photoelectric conversion unit 20 is directly supported by a support substrate 70 is shown as an example. In other words, in the example shown in FIG. 1, the reflection layer 60, the intermediate layer 50, and the active layer 40 are stacked in the given order on the support substrate 70. Also, in FIG. 4, a mode in which the photoelectric conversion unit 20 is indirectly (i.e., via another layer provided therebetween) supported by a support substrate 71 is shown as an example. A Si substrate, a glass substrate (e.g., a quartz glass substrate), and a $TiO_2$ single crystal substrate can be given as examples of the support substrate 70 and the support substrate 71. Note that the $TiO_2$ single crystal substrate is a $TiO_2$ single-crystal substrate doped with Nb, for example.

The active layer 40 includes a plasmonic material, which is a material in which plasmon resonance occurs due to a reciprocal action with the light to be converted. The light to be converted is, for example, light in the wavelength range of visible light, or light in the wavelength range of near-infrared light. A metal, a metal nitride, or a metal oxide can be used as the plasmonic material, for example. Au, Ag, Al, Cu, Pt, and Pd can be given as examples of metals used as plasmonic materials. TiN can be given as an example of a metal nitride used as a plasmonic material. ITO (indium tin oxide), FTO (fluorine-doped tin oxide), and ZnO doped with another element (aluminum, gallium, or the like) can be given as examples of metal oxides used as plasmonic materials. Hereinafter, ITO, FTO, and ZnO doped with another element will be collectively referred to as "transparent conducting materials" in some cases. It is also possible to use a compound material obtained by combining multiple types of materials as the plasmonic material. The thickness of the active layer 40 is set to be a value in a range in which a portion of the light to be converted reaches the end portion on the side from which the light to be converted is emitted in the active layer 40, or in other words, a value in a range in which a portion of the light to be converted is transmitted by the active layer 40. The thickness of the active layer 40 is set to be a thickness included in a range of 400 nm or less, for example.

When light with a wavelength capable of generating localized surface plasmon resonance in the active layer 40 is incident on the active layer 40, absorption and scattering of light occur due to the localized surface plasmon resonance. If the wavelength at which absorbance is at its maximum (peak wavelength of the absorbance spectrum) is set as the plasmon resonance wavelength in the wavelength range of the light capable of generating localized surface plasmon resonance in the active layer 40, the plasmon resonance wavelength can be controlled by the type of the plasmonic material, the shape of the structure (as will be described later, the plasmonic particles in the present embodiment) formed by the plasmonic material, the dimensions of the structure formed by the plasmonic material, the separation distance between the structures formed by the plasmonic material, and the like. For example, the plasmon resonance wavelength generally shifts to a shorter wavelength as the particle diameter of the plasmonic particles decreases. Also, for example, the plasmon resonance wavelength generally shifts to a shorter wavelength as the shape of the plasmonic particles becomes more spherical.

The intermediate layer 50 has both a semiconductor property and transparency with respect to the light to be converted. In the present embodiment, the intermediate layer 50 is a flat plate-shaped layer. Here, "having a semiconductor property" means, if the categories of "conductor", "semiconductor" and "insulator" are set according to electrical conductivity in the stated order starting from a high electrical conductivity, having an electrical conductivity classified as that of the "semiconductor". For example, it is possible to assume that a semiconductor property is included if the electrical conductivity at room temperature falls within a range of $10^{-6}$ S/m or more and $10^{6}$ S/m or less. Due to the intermediate layer 50 having a semiconductor property, electrons in the intermediate layer 50 can move to generate electrical energy. Also, "having transparency with respect to the light to be converted" means that the transmittance with respect to the light to be converted is 40% or more. Transmittance in this context means the transmittance at a wavelength at which the transmittance is at its maximum in the wavelength range of the light to be converted. Note that the transmittance with respect to the light to be converted of the intermediate layer 50 is preferably 50% or more, and more preferably 60% or more. The thickness of the intermediate layer 50 is set to be a thickness that falls within a range of 10 nm or more and 500 μm or less, for example.

For example, a metal oxide (oxide semiconductor) or a conducting polymer (polymer semiconductor) can be used as the material forming the intermediate layer 50 (intermediate layer forming material). Examples of metal oxides used as the intermediate layer forming material include $TiO_2$, ZnO, $SnO_2$, NiO, and $VO_2$. For example, $TiO_2$ is preferably used as the intermediate layer forming material.

A metal oxide with improved conductivity due to doping with another element or oxygen deficiency can be used as the metal oxide used as the intermediate layer forming material. For example, $TiO_2$ doped with a group V element (Nb, etc.) can be used as the intermediate layer forming material. In this case, from the viewpoint of maintaining the semiconductor property of the intermediate layer 50, the content of the group V element (Nb, etc.) is preferably 1 wt % or less. Also, for example, $TiO_{2-x}$ that has oxygen deficiency can be used as the intermediate layer forming material. In this case, from the viewpoint of maintaining the semiconductor property of the intermediate layer 50, "X" of $TiO_{2-x}$ is preferably 0.5 or less. A compound material in which multiple types of materials are combined can also be used as the intermediate layer forming material.

The reflection layer 60 has reflectivity with respect to the light to be converted. In the present embodiment, the reflection layer 60 is a flat plate-shaped layer. Here, "having reflectivity with respect to the light to be converted" means that the reflectance with respect to the light to be converted is 40% or more. Reflectance in this context means the reflectance at a wavelength at which the reflectance is at its maximum in the wavelength range of the light to be converted. Note that the reflectance with respect to the light to be converted of the reflection layer 60 is preferably 60% or more and more preferably 80% or more. The thickness of the reflection layer 60 is, for example, a thickness that falls within a range of 10 nm or more and several μm or less.

For example, a metal or a metal nitride can be used as the material forming the reflection layer 60 (reflection layer forming material). Au, Ag, Al, Cu, and Pt can be given as examples of metals used as the reflection layer forming material. Also, TiN can be given as an example of a metal nitride used as a reflection layer forming material. The same material as the plasmonic material included in the active layer 40 (in a later-described Working Example, Au) can also be used as the reflection layer forming material. A compound material in which multiple types of materials are combined can also be used as the reflection layer forming material.

The photoelectric conversion unit 20 uses the surface plasmon resonance (i.e., localized surface plasmon resonance) that occurs in the active layer 40 to convert the light energy of the light to be converted, into electrical energy. Specifically, the electrical energy is generated due to electrons moving from one of the active layer 40 and the intermediate layer 50 to the other due to absorption of the light to be converted in the active layer 40. By strengthening the reciprocal action between the light to be converted that is incident on the active layer 40 and the plasmonic material included in the active layer 40, the percentage of the light to be converted that is absorbed in the active layer 40 can be increased. In this respect, the photoelectric conversion unit 20 includes the reflection layer 60, which has reflectivity with respect to the light to be converted, on the side of the active layer 40 from which the light to be converted is emitted. Also, the intermediate layer 50 arranged between the active layer 40 and the reflection layer 60 has transparency with respect to the light to be converted. For this reason, the light to be converted that has passed through the active layer 40 can be caused to be incident once again on the active layer 40 by being reflected by the reflection layer 60, and the reciprocal action between the light to be converted and the plasmonic material included in the active layer 40 can be strengthened accordingly. At this time, the thickness of the intermediate layer 50 is set appropriately with consideration given to interference caused by multipath reflection of the light, whereby the intensity of the light (reflected light) returning from the active layer 40 to the side on which the light to be converted is incident can be suppressed to a low level. As a result, the percentage of the light to be converted that has passed through the active layer 40 and is enclosed in the intermediate layer 50 until being absorbed in the active layer 40 can be increased.

In the present embodiment, as shown in FIG. 1, the active layer 40 is a layer that has a structure (stacked body) in which plasmonic layers 40*a* and non-plasmonic layers 40*b* are stacked alternatingly in a stacking direction. Here, the plasmonic layers 40*a* are layers formed using the plasmonic material, and the non-plasmonic layers 40*b* are layers formed using a material (non-plasmonic material) that is different from the plasmonic material. The active layer 40 is a layer with a structure in which the plasmonic layers 40*a* and the non-plasmonic layers 40*b* are stacked alternatingly, and thus, unlike the case where the active layer 40 includes only a single plasmonic layer 40*a*, it is possible to achieve an increase in the percentage of the light to be converted that is absorbed in the active layer 40 by using the bonding effect of surface plasmons between the different plasmonic layers 40*a*. For example, a metal oxide can be used as the non-plasmonic material. Examples of metal oxides used as the non-plasmonic material include $TiO_2$, $ZnO$, $SnO_2$, and $SrTiO_3$. For example, $TiO_2$ is preferably used as the non-plasmonic material. The same material as the intermediate layer forming material (in a later-described Working Example, $TiO_2$) can be used as the non-plasmonic material.

The thicknesses of the plasmonic layers 40*a* and the non-plasmonic layers 40*b* can be thicknesses that fall within a range of 1 nm or more and 5 nm or less, for example. Note that as will be described later, in the present embodiment, the plasmonic layers 40*a* are layers that include multiple plasmonic particles, and the thicknesses of the plasmonic layers 40*a* can differ according to their positions in a plane orthogonal to the stacking direction. In this case, the thickness of a plasmonic layer 40*a* can be defined as the average value, maximum value, or the like of the thickness at positions in the plane orthogonal to the stacking direction, for example. If the stacking number is the total number of layers of the plasmonic layers 40*a* and the non-plasmonic layers 40*b* constituting the active layer 40, the stacking number is set to be a value within a range in which a portion of the light to be converted reaches an end portion on a side of the active layer 40 from which the light to be converted is emitted. The stacking number is a value that falls within a range of 20 or less, for example. In the present embodiment, as shown in FIG. 1, the bottom layer (layer closest to the side from which the light to be converted is emitted) of the stacked body constituting the active layer 40 is a plasmonic layer 40*a*, and the top layer (layer closest to the side on which the light to be converted is incident) of the stacked body constituting the active layer 40 is a plasmonic layer 40*a*. Accordingly, in the present embodiment, the stacking number is an odd number. In the example shown in FIG. 1, the stacking number is "15".

Also, in the present embodiment, layers including multiple plasmonic particles are used as the plasmonic layers 40*a* so as to achieve an increase in the reciprocal action between the light to be converted and the plasmonic material included in the active layer 40. Here, the plasmonic particles are minute particles that include the plasmonic material, and for example, minute particles composed of the plasmonic material are used. The particle diameter of the plasmonic particles is set to a particle diameter in the order of nanometers (1 nm to 100 nm) or in the order of sub-microns (100 nm to 1 μm), for example. In the present embodiment, the multiple plasmonic particles included in the plasmonic layers 40*a* are arranged two-dimensionally in a dispersed manner along the plane orthogonal to the stacking direction. The arrangement of the multiple plasmonic particles along the plane may be regular or irregular. The multiple plasmonic particles are generally arranged apart from each other. It is also possible to use a configuration in which the plasmonic layers 40*a* are formed using both a plasmonic material and a non-plasmonic material, and for example, it is possible to use a configuration in which the non-plasmonic material exists in the entirety or a portion of the gap between the plasmonic particles in the plasmonic layers 40*a* or a configuration in which the plasmonic particles are covered by the non-plasmonic material.

Figure 2:
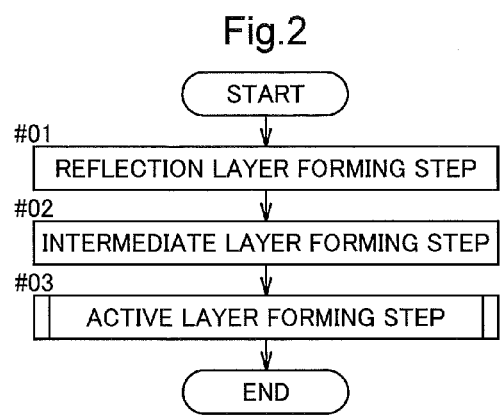
FIG. 2 is a flowchart showing an example of a method for manufacturing a photoelectric conversion unit according to an embodiment.

Next, a method for manufacturing the photoelectric conversion unit according to the present embodiment will be described. As shown in FIG. 2, the method for manufacturing the photoelectric conversion unit according to the present embodiment includes a reflection layer forming step (step #01), an intermediate layer forming step (step #02), and an active layer forming step (step #03). In the present embodiment, the reflection layer forming step (step #01), the intermediate layer forming step (step #02), and the active layer forming step (step #03) are executed in the stated order.

The reflection layer forming step (step #01) is a step of forming the reflection layer 60 on a support substrate or on another layer (in the example shown in FIG. 4, second electrode 32) supported by the support substrate. The reflection layer forming step is a step in which the reflection layer forming material is deposited through sputtering, for example. The intermediate layer forming step (step #02) is a step of forming the intermediate layer 50 on the reflection layer 60. The intermediate layer forming step is a step in which the intermediate layer forming material is deposited through sputtering, for example. The active layer forming step (step #03) is a step of forming the active layer 40 on the intermediate layer 50.

Figure 3:
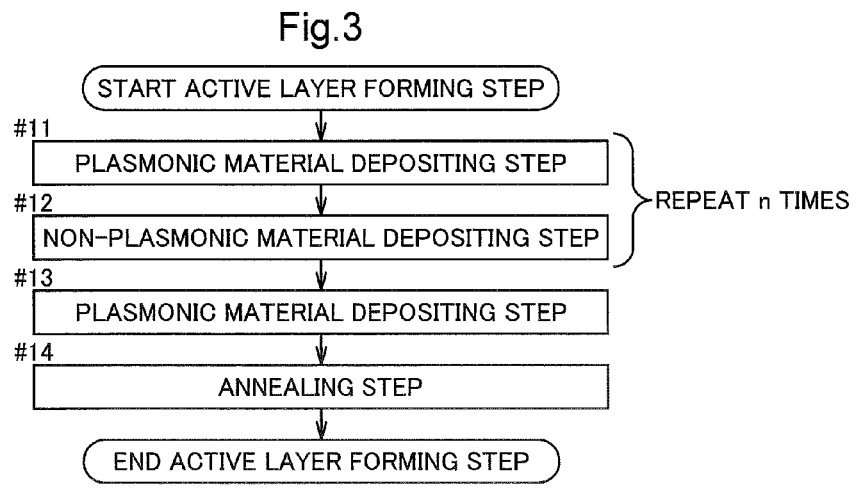
FIG. 3 is a flowchart showing an example of an active layer forming step according to an embodiment.

As shown in FIG. 3, the active layer forming step according to the present embodiment includes plasmonic material depositing steps (step #11, step #13), a non-plasmonic material depositing step (step #12), and an annealing step (step #14). In the present embodiment, a step of executing the plasmonic material depositing step (step #11) and thereafter executing the non-plasmonic material depositing step (step #12) is repeatedly executed n times, and thereafter the plasmonic material depositing step (step #13) and the annealing step (step #14) are executed in the stated order. The value of "n" is the value of the integer portion of half of the above-described stacking number (half of the value obtained by subtracting "1" from the stacking number). The plasmonic material depositing steps (step #11, step #13) are steps of forming the plasmonic layers 40*a* by depositing the plasmonic material. The plasmonic material depositing steps are steps in which the plasmonic material is deposited through sputtering, for example. The non-plasmonic material depositing step (step #12) is a step of forming the non-plasmonic layer 40*b* by depositing the non-plasmonic material. The non-plasmonic material depositing step is a step in which the non-plasmonic material is deposited through sputtering, for example. The annealing step (step #14) is a step in which annealing processing is used to make a thin film deposited through the plasmonic material depositing step into particles and change the plasmonic layers 40*a* into layers including multiple plasmonic particles.

2. Configuration of Wavelength Sensor

As shown in FIG. 4, the wavelength sensor 1 according to the present embodiment includes the photoelectric conversion element 10 and a wavelength information output unit 2 that is electrically connected to the photoelectric conversion element 10. In the example shown in FIG. 4, the photoelectric conversion element 10 includes a pair of electrodes 30, namely a first electrode 31 and a second electrode 32, and the photoelectric conversion unit 20 of the photoelectric conversion element 10 includes an electric charge movement layer 80 on the side of the active layer 40 on which the light to be converted is incident. In this example, the photoelectric conversion unit 20 of the photoelectric conversion element 10 is arranged between the pair of electrodes 30. Also, in the example shown in FIG. 4, an insulating layer 4 is formed on the surface of the support substrate 71, and the second electrode 32, the reflection layer 60, the intermediate layer 50, the active layer 40, the electric charge movement layer 80, and the first electrode 31 are stacked in the stated order on a wiring layer 3 formed so as to be exposed on the surface of the insulating layer 4.

The electrodes 30 are formed using conductive materials. For example, a metal or a metal oxide can be used as the material forming the electrodes 30 (electrode forming material). Au, Ag, Cu, Pt, and Pd can be given as examples of metals used as electrode forming materials. Also, ITO and FTO can be given as examples of metal oxides used as electrode forming materials. Note that in the example shown in FIG. 4, the light to be converted passes through the first electrode 31 and the electric charge movement layer 80 to be incident on the active layer 40, and therefore the first electrode 31 needs to have transparency with respect to the light to be converted, as well as conductivity. Accordingly, the first electrode 31 is formed using a transparent conductive material such as ITO or FTO, for example. It is possible to use a configuration in which the second electrode 32 is formed using the same material as the reflection layer forming material, and in this case, the reflection layer 60 may also include the function of the second electrode 32.

The electric charge movement layer 80 is a layer in which the electric charge moves between the first electrode 31 and the active layer 40 when the light energy is converted into electrical energy. The electric charge movement layer 80 is, for example, a layer including an electrolyte (e.g., a liquid electrolyte, gel electrolyte, or the like) that includes a redox species, or a hole transport layer in which a p-type semiconductor is used. For example, it is possible to use one or both of a halogen and a metal as the redox species. Cl, Br, and I can be given as examples of halogens used as the redox species, and Na, K, and Fe can be given as examples of metals used as the redox species. Also, $CuAlO_2$ and CuNbO can be given as examples of p-type semiconductors used as hole transport layers. Note that in the example shown in FIG. 4, the light to be converted passes through the first electrode 31 and the electric charge movement layer 80 to be incident on the active layer 40, and therefore the electric charge movement layer 80 needs to have transparency with respect to the light to be converted. Accordingly, if the electric charge movement layer 80 is the hole transport layer, the hole transport layer is formed using a p-type semiconductor (p-type transparent conducting oxide) such as $CuAlO_2$ or CuNbO, for example.

A specific wavelength is used as a boundary wavelength, and the wavelength information output unit 2 outputs different signals in the case where the wavelength of the light to be converted is longer than the boundary wavelength, and in the case where the wavelength of the light to be converted is shorter than the boundary wavelength. Accordingly, if the light to be converted is monochromatic light or light that is nearly monochromatic, it is possible to determine based on the output signal of the wavelength information output unit 2 whether the light to be converted is light with a wavelength longer than the boundary wavelength or light with a wavelength shorter than the boundary wavelength.

The wavelength information output unit 2 outputs the above-described signal based on a phenomenon in which the movement direction of the electrons in the photoelectric conversion unit 20 when the light to be converted is incident on the active layer 40 changes according to the wavelength of the light to be converted. Although this phenomenon will be described in later Working Examples, in the photoelectric conversion unit 20 according to the present embodiment, if the wavelength of the light to be converted is longer than a specific wavelength, the movement direction of the electrons inside of the photoelectric conversion unit 20 becomes a direction of moving from the active layer 40 to the intermediate layer 50, and if the wavelength of the light to be converted is shorter than the specific wavelength, the movement direction of the electrons inside of the photoelectric conversion unit 20 becomes a direction of moving from the intermediate layer 50 to the active layer 40. Here, the "specific wavelength" is a wavelength that is shorter than the plasmon resonance wavelength. Accordingly, with the wavelength sensor 1 configured as shown in FIG. 4, if the wavelength of the light to be converted is longer than the specific wavelength, a flow of electrons moving from the second electrode 32 to the external circuit (wavelength information output unit 2) is formed, and if the wavelength of the light to be converted is shorter than the specific wavelength, a flow of electrons moving from the external circuit (wavelength information output unit 2) to the second electrode 32 is formed. The wavelength information output unit 2 includes a circuit component that outputs mutually different signals (e.g., two signals with different voltages) according to this difference in the moving directions of the electrons (i.e., according to the difference in the direction in which the current flows). The circuit component is a rectifier, a comparator, or the like, for example. Accordingly, using the specific wavelength as a boundary wavelength, the wavelength information output unit 2 outputs mutually different signals in the case where the wavelength of the light to be converted is longer than the boundary wavelength and in the case where the wavelength of the light to be converted is shorter than the boundary wavelength. Note that the phenomenon that is used in order to detect whether the wavelength of the light to be detected is longer than or shorter than the boundary wavelength is the difference in the directions of the current, and the direction of the current can generally be detected using a simpler configuration compared to that used in the case of detecting the magnitude of the current, or the like. Accordingly, it is possible to achieve simplification of the configuration (e.g., the configuration of the circuit component) of the wavelength information output unit 2. Note that as will be described later, in a state with zero bias, the specific wavelength is shorter than the plasmon resonance wavelength, but by applying a bias voltage, it is possible to set the specific wavelength to be about the same as the plasmon resonance wavelength, and to set the specific wavelength to be longer than the plasmon resonance wavelength. Accordingly, the boundary wavelength can also be set to be about the same as the plasmon resonance wavelength and to be longer than the plasmon resonance wavelength.

3. Working Examples

Hereinafter, working examples of the photoelectric conversion unit (photoelectric conversion element) will be described. Note that the photoelectric conversion unit (photoelectric conversion element) according to the present disclosure is not limited by the following working examples.

3-1. Working Example 1

A photoelectric conversion unit 20 with the structure shown in FIG. 1 was produced according to the procedure shown in FIGS. 2 and 3, using a $TiO_2$ single crystal substrate as the support substrate 70, Au as the plasmonic material and the reflection layer forming material, and $TiO_2$ as the non-plasmonic material and the intermediate layer forming material. In other words, in the present working example, the plasmonic material is gold, the intermediate layer is formed using titanium oxide, and the reflection layer is formed using gold. Specifically, a reflection layer 60 with a thickness of 200 nm was formed on the support substrate 70 through sputtering of Au. Next, an intermediate layer 50 with a thickness of 100 nm was formed on the reflection layer 60 through sputtering of $TiO_2$. Next, sputtering of Au and sputtering of $TiO_2$ were performed alternatingly so as to form, on the intermediate layer 50, an active layer 40 having a structure in which plasmonic layers 40a with thicknesses of 2 nm and non-plasmonic layers 40b with thicknesses of 3 nm were stacked alternatingly. Here, as shown in FIG. 1, an active layer 40 with a stacking number of "15", that is, an active layer 40 including eight plasmonic layers 40a and seven non-plasmonic layers 40b was formed. Also, annealing processing in an argon atmosphere was performed for one hour at 800° C. so as to change the plasmonic layers 40a into layers including multiple plasmonic particles. A photoelectric conversion unit 20 with the structure shown in FIG. 1 was produced using the above-described steps.

Using the produced photoelectric conversion unit 20, the photocurrent that is generated due to photoelectric conversion performed by the photoelectric conversion unit 20 was measured. Specifically, a measurement circuit was formed in which the photoelectric conversion unit 20 is used as a working electrode, an electrode made of Pt is used as a counter electrode, and a calomel electrode is used as a reference electrode. Then, an electrochemical analyzer was used to measure the photocurrent that flows between the working electrode and the counter electrode in the case of switching every 5 seconds between a state in which light is incident on the active layer 40 and a state in which light is not incident on the active layer 40. Note that the photoelectric conversion unit 20 and the electrochemical analyzer were connected by an electrode provided on a surface on a side of the support substrate 70 opposite to that of the reflection layer 60. Also, a $KClO_4$ aqueous solution was used as an electrolytic solution, and the working electrode (surface on the side of the active layer 40 opposite to that of the intermediate layer 50), the counter electrode, and the reference electrode were immersed in the electrolytic solution.

Figure 5:
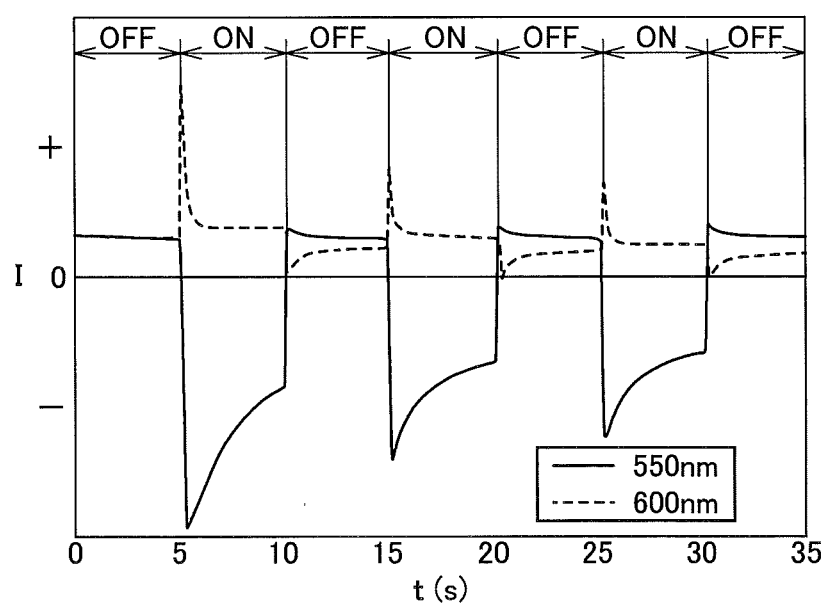
FIG. 5 is a diagram showing a result of measuring the time responsiveness of a photocurrent of a photoelectric conversion unit according to Working Example 1.

The results of measuring the photocurrent in the case where the wavelength of the light incident on the active layer 40 is 550 nm and in the case where the wavelength is 600 nm are shown in FIG. 5. The vertical axis in FIG. 5 indicates the photocurrent (I), and the horizontal axis in FIG. 5 indicates the time (t). Note that a xenon lamp was used as a light source, and the wavelength of the light incident on the active layer 40 was switched using a band-pass filter. From FIG. 5, it can be understood that if light with a wavelength of 600 nm is incident on the active layer 40, a positive photocurrent flows, whereas if light with a wavelength of 550 nm is incident on the active layer 40, a negative photocurrent flows. Note that the positive photocurrent corresponds to the case where electrons flow from the active layer 40 to the intermediate layer 50 in the photoelectric conversion unit 20, and the negative photocurrent corresponds to the case where electrons flow from the intermediate layer 50 to the active layer 40 in the photoelectric conversion unit 20.

Figure 6:
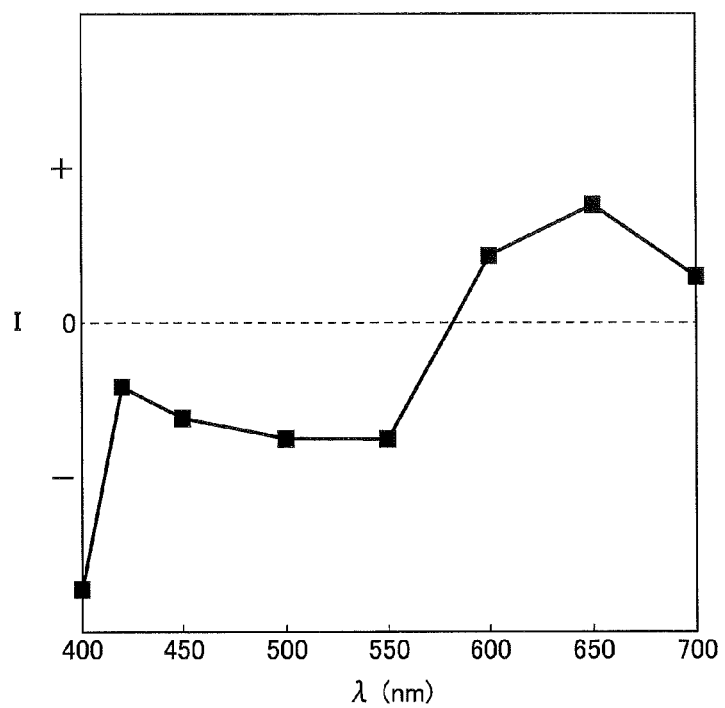
FIG. 6 is a diagram showing a result of measuring the wavelength dependence of a photocurrent of a photoelectric conversion unit according to Working Example 1.

FIG. 6 is a diagram showing the results of measuring the wavelength dependence of incident light for photocurrents obtained through the above-described measurement. Note that the vertical axis in FIG. 6 indicates the current (net current) obtained by subtracting the current value before emission of light (dark current value) from the current value after emission of light. That is, the vertical axis of FIG. 6 indicates the photocurrent (I), and the horizontal axis of FIG. 6 indicates the wavelength (λ) of the incident light. From FIG. 6, it can be understood that the directions of the photocurrents are opposite in the case where the wavelength of the light to be converted is longer than the specific wavelength (in this example, a wavelength between 550 nm and 600 nm) and the case where the wavelength of the light to be converted is shorter than the specific wavelength. By using this phenomenon, it is possible to realize the above-described wavelength sensor 1. If the photoelectric conversion unit 20 shown in the present working example is used as the wavelength sensor 1, mainly light in the visible region will be used as the light to be converted.

3-2. Working Example 2

A photoelectric conversion unit 20 was produced using a method and materials similar to those used in Working Example 1, except that the thickness of the intermediate layer 50 formed in the intermediate layer forming step was 25 nm, the thickness of each plasmonic layer 40a formed in the plasmonic material depositing step was 3 nm, the thickness of each non-plasmonic layer 40b formed in the non-plasmonic material depositing step was 10 nm, and annealing processing in a dry air atmosphere was performed for one hour at 450° C. as the annealing step. Then, a measurement circuit similar to that in Working Example 1 was formed, and the photocurrent and photovoltage generated due to the photoelectric conversion performed by the photoelectric conversion unit 20 were measured.

Figure 7:
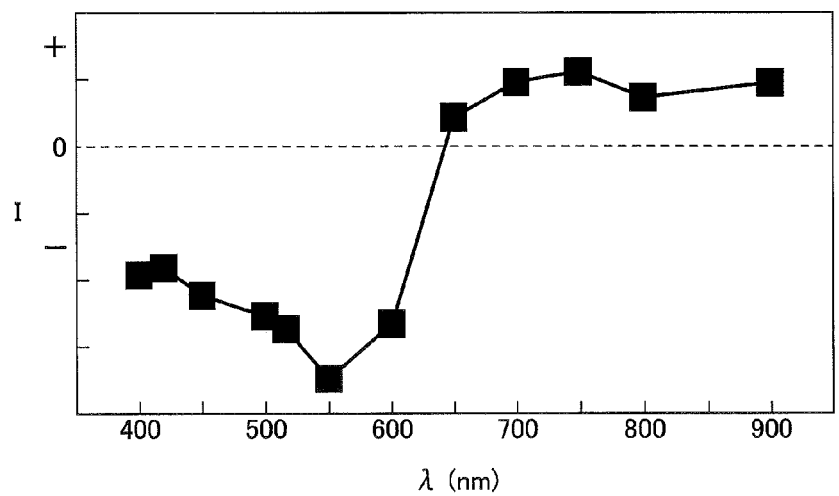
FIG. 7 is a diagram showing a result of measuring the wavelength dependence of a photocurrent of a photoelectric conversion unit according to Working Example 2.
Figure 8:
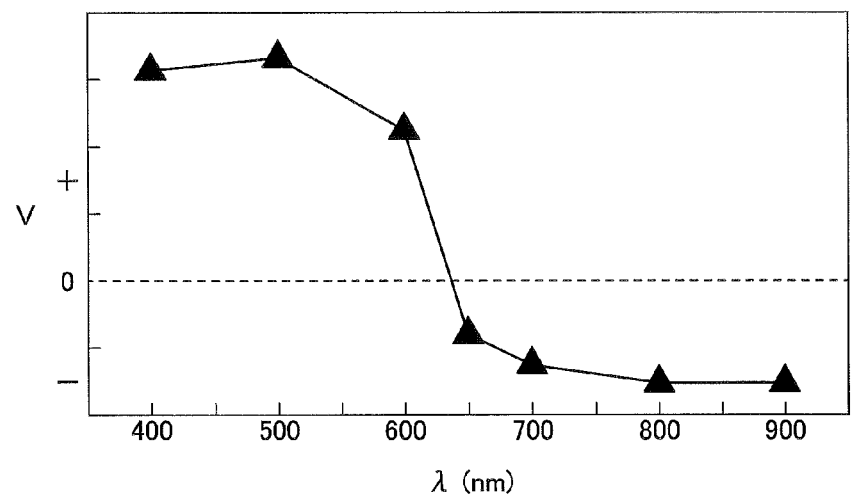
FIG. 8 is a diagram showing a result of measuring the wavelength dependence of a photovoltage of a photoelectric conversion unit according to Working Example 2.

FIG. 7 shows results of measuring the wavelength dependence of incident light with respect to the photocurrent, and FIG. 8 shows results of measuring the wavelength dependence of incident light with respect to the photovoltage. Note that the vertical axis of FIG. 7 indicates the net current, similarly to the vertical axis of FIG. 6. That is, the vertical axis of FIG. 7 indicates the photocurrent (I), and the horizontal axis of FIG. 7 indicates the wavelength (λ) of the incident light. Also, the vertical axis of FIG. 8 indicates the voltage (release voltage) between the working electrode and the counter electrode. That is, the vertical axis of FIG. 8 indicates the photovoltage (V), and the horizontal axis of FIG. 8 indicates the wavelength (λ) of the incident light. From FIG. 7, it can be understood that in the photoelectric conversion unit 20 of Working Example 2, the specific wavelength is around 650 nm, which is longer than the specific wavelength of the photoelectric conversion unit 20 of Working Example 1 (see FIG. 6). Also, from FIGS. 7 and 8, it can be understood that the direction of the photocurrent switches in correspondence with the direction (sign) of the photovoltage switching at the specific wavelength.

3-3. Working Example 3

Four photoelectric conversion units 20 were produced using procedures and materials similar to those used in Working Example 2, excluding the thickness of each plasmonic layer 40a formed in the plasmonic material depositing step. Specifically, a photoelectric conversion unit 20 in which the thickness of each plasmonic layer 40a formed in the plasmonic material depositing step is 1 nm, a photoelectric conversion unit 20 in which the thickness of each plasmonic layer 40a formed in the plasmonic material depositing step is 2 nm, a photoelectric conversion unit 20 in which the thickness of each plasmonic layer 40a formed in the plasmonic material depositing step is 3 nm (a photoelectric conversion unit 20 similar to that of Working Example 2), and a photoelectric conversion unit 20 in which the thickness of each plasmonic layer 40a formed in the plasmonic material depositing step is 5 nm were produced. Also, a measurement circuit similar to that of Working Example 1 was formed, and the photocurrent that is generated by the photoelectric conversion performed by the photoelectric conversion unit 20 was measured in each of the four photoelectric conversion units 20.

Figure 9:
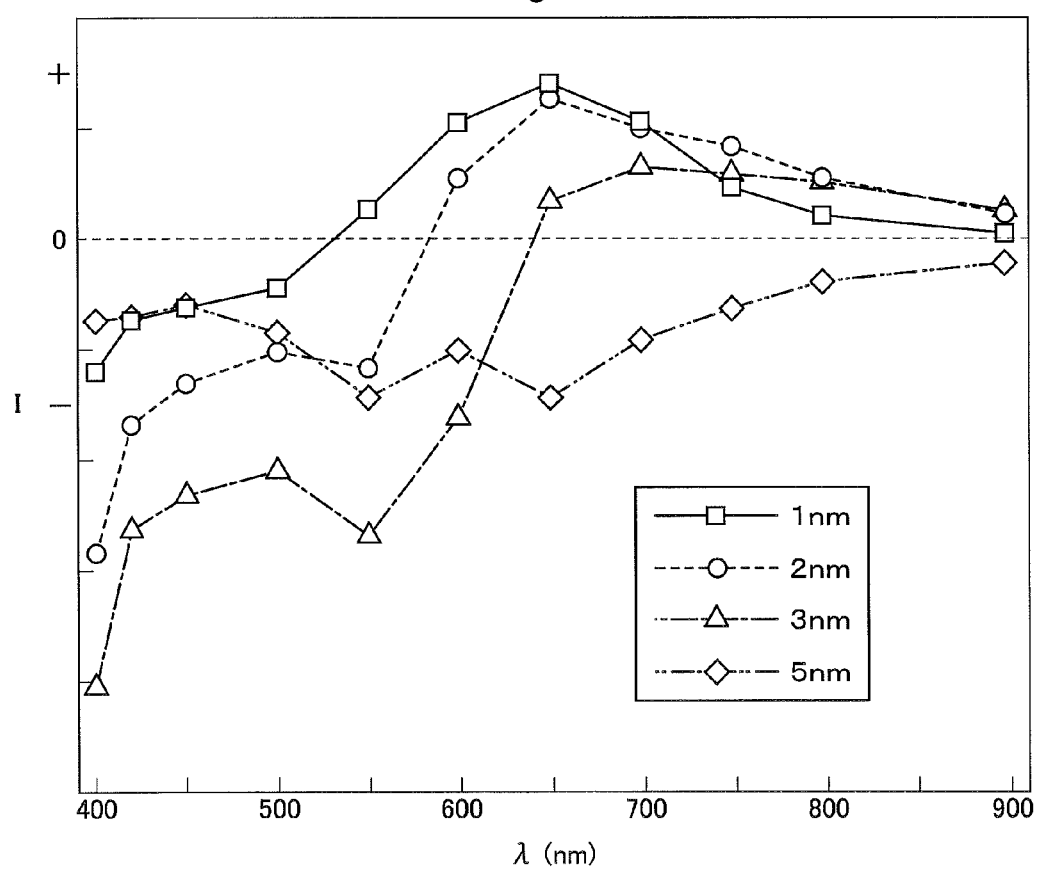
FIG. 9 is a diagram showing a result of measuring the wavelength dependence of a photocurrent of a photoelectric conversion unit according to Working Example 3.

FIG. 9 shows results of measuring the wavelength dependence of incident light with respect to the photocurrent. Note that the vertical axis of FIG. 9 indicates the net current, similarly to the vertical axis of FIG. 6. That is, the vertical axis of FIG. 9 indicates the photocurrent (I), and the horizontal axis of FIG. 9 indicates the wavelength (λ) of the incident light. Also, the numerical values in the explanatory notes shown in FIG. 9 indicate the thicknesses of each plasmonic layer 40a formed in the plasmonic material depositing step. From FIG. 9, it can be understood that the specific wavelength, which is the wavelength at which the direction of the photocurrent switches (wavelength at which photocurrent switching occurs), shifts to the long wavelength side (in this example, from the visible light region to the near-infrared light region) as the thickness of each plasmonic layer 40a increases. Specifically, the specific wavelength is 540 nm for the photoelectric conversion unit 20 in which the thickness of each plasmonic layer 40a is 1 nm, and the specific wavelength is 650 nm for the photoelectric conversion unit 20 in which the thickness of each plasmonic layer 40a is 3 nm.

3-4. Working Example 4

A photoelectric conversion unit 20 was produced using a method and materials similar to those used in Working Example 2, except that the support substrate 70 was an FTO substrate. Then, a measurement circuit similar to that in Working Example 1 was formed, and the photocurrent and photovoltage generated due to the photoelectric conversion performed by the photoelectric conversion unit 20 were measured.

Figure 10:
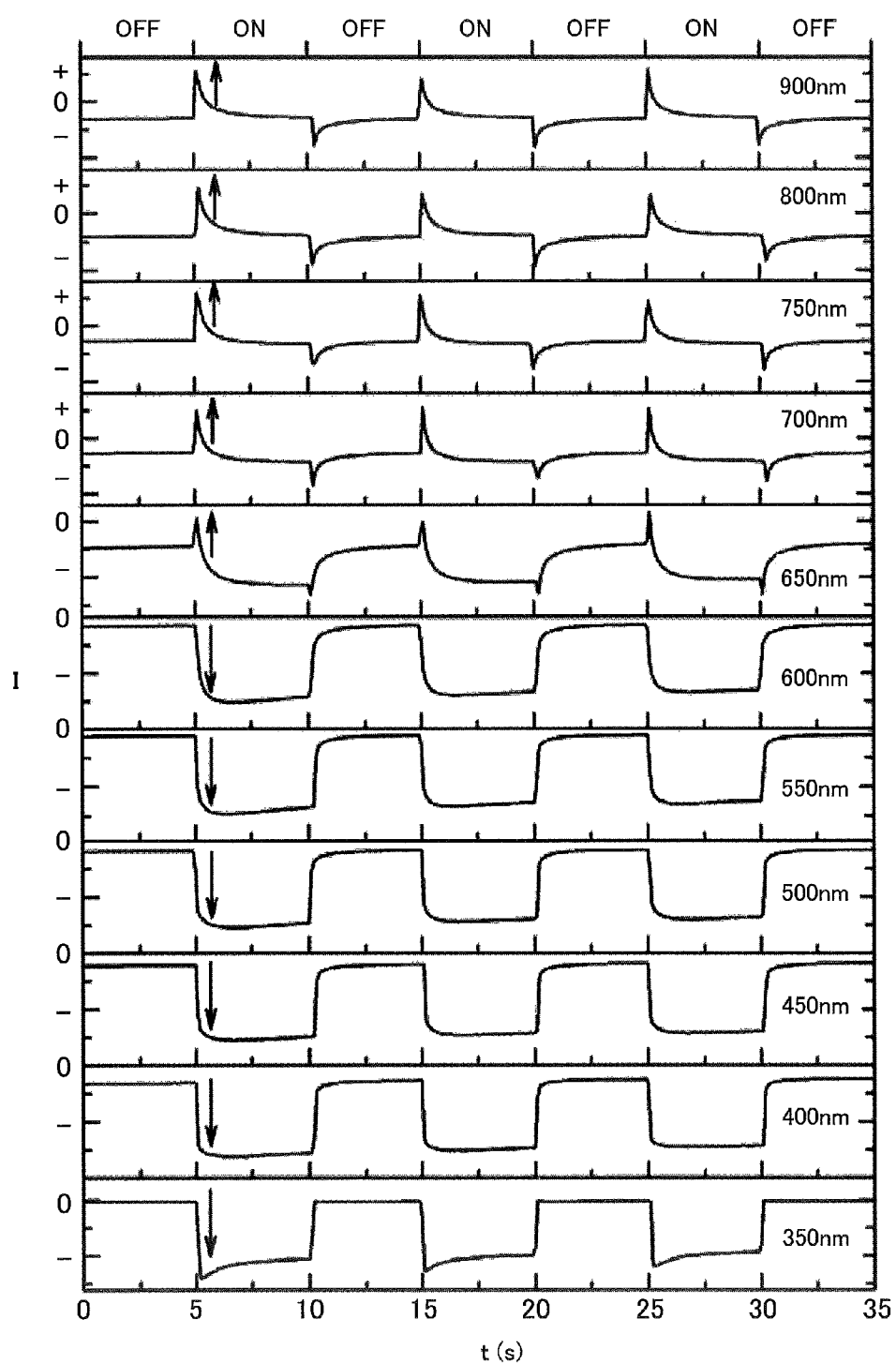
FIG. 10 is a diagram showing a result of measuring the time responsiveness of a photocurrent of a photoelectric conversion unit according to Working Example 4.

FIG. 10 shows the results of measuring the photocurrent that flows between the working electrode and the counter electrode in the case of switching every 5 seconds between a state in which light is incident on the active layer 40 and a state in which light is not incident on the active layer 40. The vertical axis in FIG. 10 indicates the photocurrent (I), and the horizontal axis in FIG. 10 indicates the time (t). Note that the wavelengths of the incident lights corresponding to the graphs are indicated on the right side of FIG. 10. From FIG. 10, it can be understood that if light with a wavelength of 600 nm or less is incident on the active layer 40, a negative photocurrent will flow (see the downward arrows in FIG. 10), whereas if light with a wavelength of 650 nm or more is incident on the active layer 40, a positive photocurrent will flow for at least a short period of time after the start of emission of light (see the upward arrows in FIG. 10). In other words, it can be understood that in the photoelectric conversion unit 20 of Working Example 4, the wavelength at which switching of the photocurrent occurs (specific wavelength) is around 650 nm (specifically, a wavelength between 600 nm and 650 nm).

Figure 11:
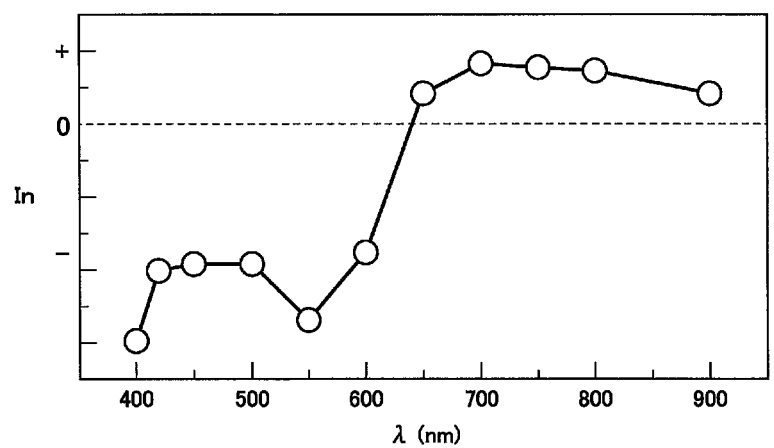
FIG. 11 is a diagram showing a result of measuring the wavelength dependence of a photocurrent of a photoelectric conversion unit according to Working Example 4.
Figure 12:
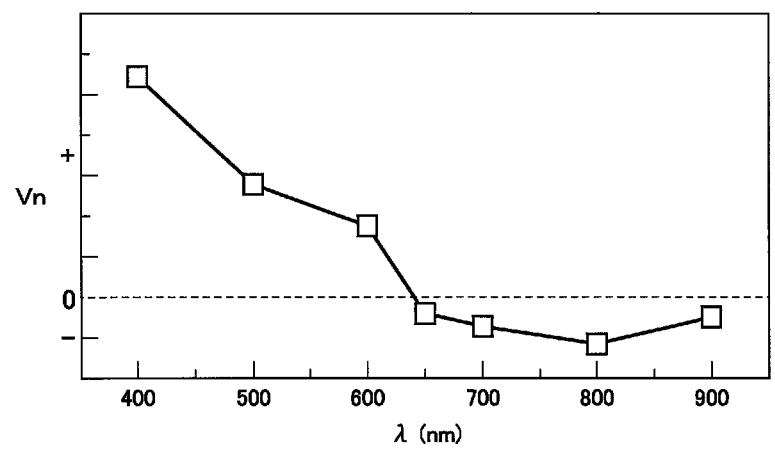
FIG. 12 is a diagram showing a result of measuring the wavelength dependence of a photovoltage of a photoelectric conversion unit according to Working Example 4.

FIG. 11 shows results of measuring the wavelength dependence of incident light with respect to the photocurrent, and FIG. 12 shows results of measuring the wavelength dependence of incident light with respect to the photovoltage. Note that the vertical axis of FIG. 11 indicates the net current normalized by the intensity of the incident light at each wavelength. That is, the vertical axis of FIG. 11 indicates the normalized photocurrent (In), and the horizontal axis of FIG. 11 indicates the wavelength (λ) of the incident light. Also, the vertical axis of FIG. 12 indicates the release voltage normalized by the intensity of the incident light at each wavelength. That is, the vertical axis of FIG. 12 indicates the normalized photovoltage (Vn), and the horizontal axis of FIG. 12 indicates the wavelength (λ) of the incident light. From FIGS. 11 and 12, it can be understood that the switching of the photocurrent (sign switching) and the switching of the photovoltage occur at the same wavelength (in this example, a wavelength of around 650 nm).

3-5. Working Example 5

Six photoelectric conversion units 20 were produced using procedures and materials similar to those used in Working Example 4, excluding the thickness of each plasmonic layer 40a formed in the plasmonic material depositing step. Specifically, a photoelectric conversion unit 20 in which the thickness of each plasmonic layer 40a formed in the plasmonic material depositing step is 0.33 nm, a photoelectric conversion unit 20 in which the thickness is 0.66 nm, a photoelectric conversion unit 20 in which the thickness is 1 nm, a photoelectric conversion unit 20 in which the thickness is 2 nm, a photoelectric conversion unit 20 in which the thickness is 3 nm (a photoelectric conversion unit 20 similar to that of Working Example 4), and a photoelectric conversion unit 20 in which the thickness is 5 nm were produced. Then, a measurement circuit similar to that in Working Example 1 was formed, and the photocurrent generated due to the photoelectric conversion performed by the photoelectric conversion unit 20 was measured.

Figure 13:
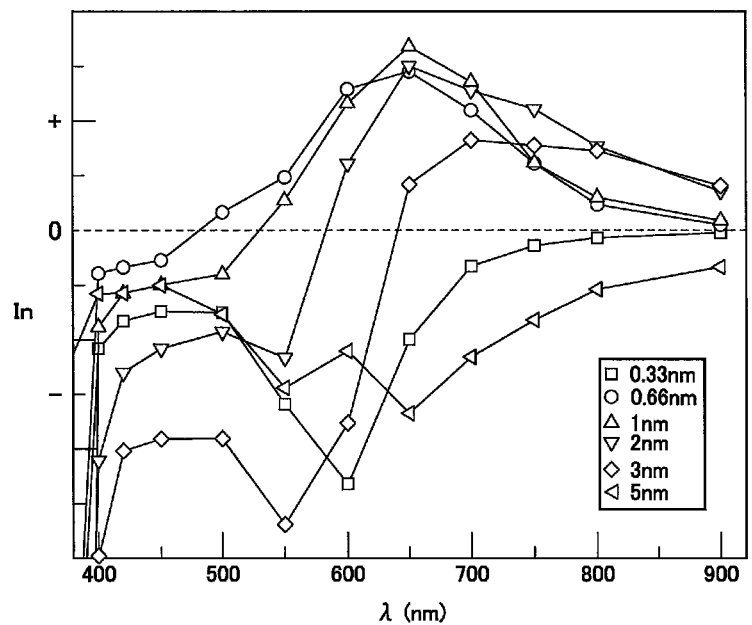
FIG. 13 is a diagram showing a result of measuring the wavelength dependence of a photocurrent of a photoelectric conversion unit according to Working Example 5.

FIG. 13 shows results of measuring the wavelength dependence of incident light with respect to the photocurrent. Note that the vertical axis of FIG. 13 indicates the normalized net current, similarly to the vertical axis of FIG. 11. That is, the vertical axis of FIG. 13 indicates the normalized photocurrent (In), and the horizontal axis of FIG. 13 indicates the wavelength (λ) of the incident light. Also, the numerical values in the explanatory note shown in FIG. 13 indicate the thicknesses of each plasmonic layer 40a formed in the plasmonic material depositing step. From FIG. 13, it can be understood that although only a negative photocurrent is generated in the photoelectric conversion unit 20 in which the thickness of each plasmonic layer 40a is 0.33 nm, photocurrent switching occurs in four of the photoelectric conversion units 20, namely the photoelectric conversion unit 20 in which the thickness of each plasmonic layer 40a is 0.66 nm, the photoelectric conversion unit 20 in which the thickness is 1 nm, the photoelectric conversion unit 20 in which the thickness is 2 nm, and the photoelectric conversion unit 20 in which the thickness is 3 nm. It is understood that the wavelength at which switching occurs (specific wavelength) shifts to the longer wavelength side as the thickness increases, between 480 nm in the case where the thickness of each plasmonic layer 40a is 0.66 nm, and 650 nm in the case where the thickness of each plasmonic layer 40a is 3 nm. Note that according to FIG. 13, in the region in which the wavelength of incident light is 400 nm to 900 nm, switching of the photocurrent is not observed in the photoelectric conversion unit 20 in which the thickness of each plasmonic layer 40a is 5 nm.

Figure 14:
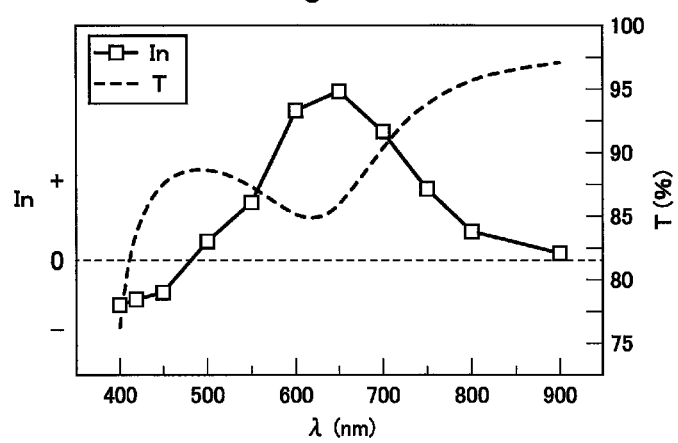
FIG. 14 is a diagram showing a result of measuring the wavelength dependence of a photocurrent and relative transmittance of a photoelectric conversion unit according to Working Example 5.
Figure 15:
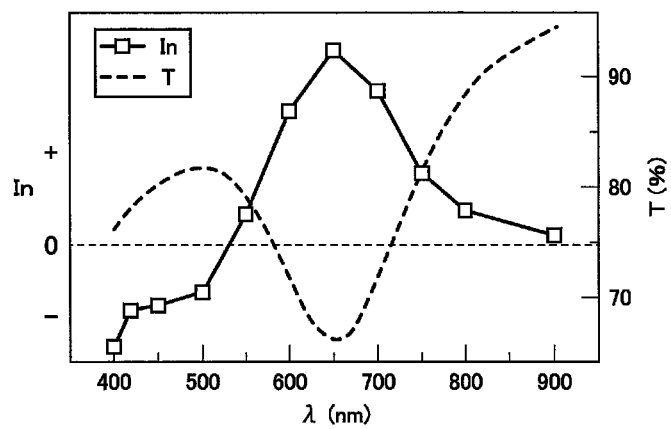
FIG. 15 is a diagram showing a result of measuring the wavelength dependence of a photocurrent and relative transmittance of a photoelectric conversion unit according to Working Example 5.
Figure 16:
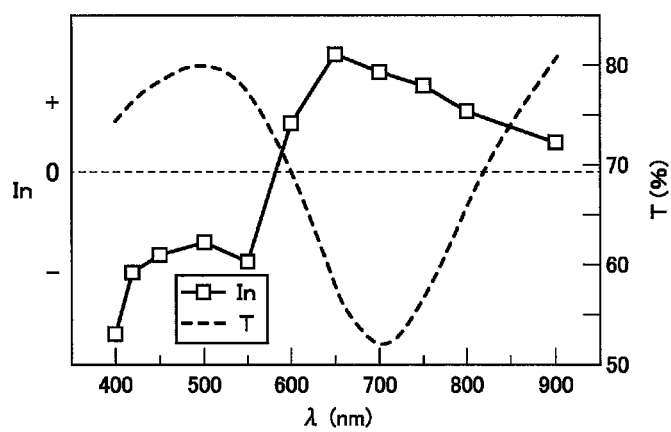
FIG. 16 is a diagram showing a result of measuring the wavelength dependence of a photocurrent and relative transmittance of a photoelectric conversion unit according to Working Example 5.
Figure 17:
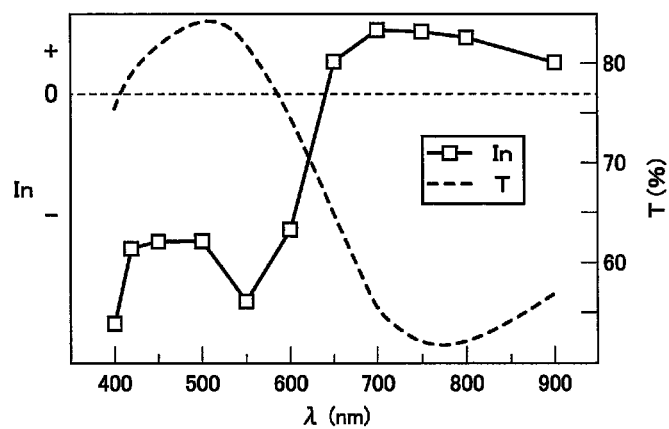
FIG. 17 is a diagram showing a result of measuring the wavelength dependence of a photocurrent and relative transmittance of a photoelectric conversion unit according to Working Example 5.

For the four photoelectric conversion units 20 in which switching of the photocurrent was observed, the results of measuring the photocurrent spectrum shown in FIG. 13 and the results of measuring the transmittance spectrum are shown overlapped in FIGS. 14 to 17. Note that FIG. 14 shows the measurement results for the photoelectric conversion unit 20 in which the thickness of each plasmonic layer 40a is 0.66 nm, FIG. 15 shows the measurement results for the photoelectric conversion unit 20 in which the thickness is 1 nm, FIG. 16 shows the measurement results for the photoelectric conversion unit 20 in which the thickness is 2 nm, and FIG. 17 shows the measurement results for the photoelectric conversion unit 20 in which the thickness is 3 nm. The transmittance spectrum is obtained by producing a photoelectric conversion unit with no reflection layer 60 (hereinafter referred to as a "sample with no reflection layer") on a glass substrate and measuring the transmittance (relative transmittance) of the sample with no reflection layer, using the glass substrate as a reference. That is, the vertical axes in FIGS. 14 to 17 indicate the normalized photocurrent (In) and the relative transmittance (T), and the horizontal axes in FIGS. 14 to 17 indicate the wavelength (λ) of the incident light. When the transmittance of the intermediate layer 50 is considered to be 100%, the relative transmittance is equal to the transmittance of the active layer 40. Note that the sample with no reflection layer was produced under the same conditions and with the same steps as those for the photoelectric conversion unit 20 on which the measurement of the photocurrent was performed, except that the reflection layer 60 was not formed.

From FIGS. 14 to 17, it can be understood that for each of the four photoelectric conversion units 20, switching of the photocurrent occurs at a wavelength that is on the shorter wavelength side (i.e., the high-energy side) with respect to the wavelength at which the transmittance is at its minimum. Here, the wavelength at which the transmittance is at its minimum corresponds to the resonance wavelength of plasmon resonance that occurs in the active layer 40. Accordingly, FIGS. 14 to 17 show that the specific wavelength at which the switching of the photocurrent occurs is shorter than the plasmon resonance wavelength. This indicates that switching of the photocurrent can occur at a wavelength that is shorter than the adjustment limit value on the short wavelength side of the plasmon resonance wavelength. Also, from FIGS. 14 to 17, it can be understood that the wavelength at which the normalized photocurrent reaches its maximum and the plasmon resonance wavelength match or approximately match.

3-6. Working Example 6

A photoelectric conversion unit 20 was produced using procedures and materials similar to those used in Working Example 4, excluding the fact that the thickness of each plasmonic layer 40a formed in the plasmonic material depositing step is 2 nm. Then, a measurement circuit similar to that in Working Example 1 was formed, and the photocurrent generated due to the photoelectric conversion performed by the photoelectric conversion unit 20 was measured. Note that the photocurrent was measured in the zero-bias state (bias voltage=0 V) as well as in a state in which a bias voltage was applied between the electrodes (between the counter electrode and the working electrode). Specifically, the photocurrent was measured under seven different bias conditions (bias voltage=+0.3 V, +0.2 V, +0.1 V, 0 V, −0.1 V, −0.3 V, and −0.5 V). Note that the sign of the bias voltage matches the sign of the voltage of the working electrode, which is determined using the counter electrode as a reference.

Figure 18:
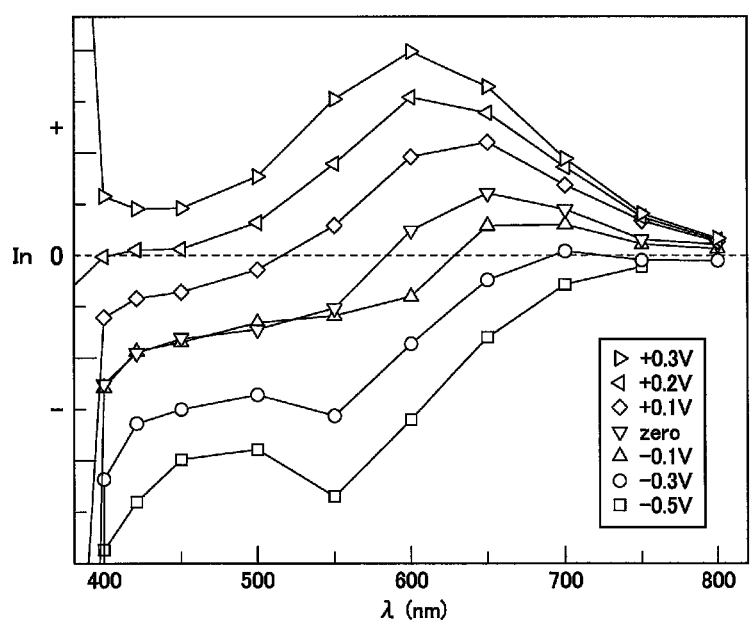
FIG. 18 is a diagram showing a result of measuring the wavelength dependence of a photocurrent of a photoelectric conversion unit according to Working Example 6.

FIG. 18 shows results of measuring the photocurrent spectrum under the different bias conditions. Note that the vertical axis of FIG. 18 indicates the normalized net current, similarly to the vertical axis of FIG. 13. That is, the vertical axis of FIG. 18 indicates the normalized photocurrent (In), and the horizontal axis of FIG. 18 indicates the wavelength (λ) of the incident light. Also, the numerical values of the explanatory note in FIG. 18 indicate the bias voltages applied when measuring the photocurrent. From FIG. 18, it can be understood that the specific wavelength at which the switching of the photocurrent occurs can be adjusted also by changing the bias voltage instead of the plasmon resonance wavelength. That is, the specific wavelength shifts to the short wavelength side as the bias voltage increases in the positive direction, and the specific wavelength shifts to the long wavelength side as the bias voltage increases in the negative direction. In the zero-bias state, the specific wavelength is shorter than the plasmon resonance wavelength, but from FIG. 18, it can be understood that by applying a bias voltage (here, a negative bias voltage), it is possible to set the specific wavelength to a wavelength that is about the same as the plasmon resonance wavelength, and to set the specific wavelength to a wavelength that is longer than the plasmon resonance wavelength.

As is evident from the above-described results of measuring the photocurrent using the produced photoelectric conversion unit 20, by using the photoelectric conversion unit 20 with the structure shown in FIG. 1, the direction of the generated photocurrent can be switched according to the wavelength of the light to be converted. Specifically, if the wavelength of the light to be converted is longer than the specific wavelength, the movement direction of the electrons inside of the photoelectric conversion unit 20 becomes the direction from the active layer 40 to the intermediate layer 50, and if the wavelength of the light to be converted is shorter than the specific wavelength, the movement direction of the electrons inside of the photoelectric conversion unit 20 becomes the direction from the intermediate layer 50 to the active layer 40. Although the details of the mechanism of this peculiar phenomenon are not clear, the following hypothesis has been made, for example. Note that the configuration of the photoelectric conversion unit (photoelectric conversion element) according to the present disclosure is not to be interpreted as being more limiting than is necessary according to the following hypothesis.

Electrons that are generated due to localized surface plasmon resonance in the active layer 40 and electrons that are generated due to excitement of surface plasmon polaritons on the surface of the reflection layer 60 (interface between the reflection layer 60 and the intermediate layer 50) are thought to be electrons that are generated inside of the photoelectric conversion unit 20 when the light to be converted is incident on the active layer 40. Note that the surface plasmon polaritons on the surface of the reflection layer 60 are excited by, for example, light that passes through the active layer 40 and the intermediate layer 50 and is directly incident on the reflection layer 60, scattered light that is generated due to Mie scattering caused by the plasmonic particles included in the active layer 40, and light that is generated in the active layer 40 due to the localized surface plasmon resonance (light that was not used in the generation of electrons in the active layer 40). The surface plasmon polaritons on the surface of the reflection layer 60 can be excited also due to a near-field effect between the active layer 40 (plasmonic particles) and the reflection layer 60. Also, a first bather at the boundary between the intermediate layer 50 and the active layer 40, a second barrier at the boundary between the intermediate layer 50 and the reflection layer 60, and a third barrier at the end portion (in the example shown in FIG. 4, the boundary between the active layer 40 and the electric charge movement layer 80) on the side of the active layer 40 opposite to the intermediate layer 50 are thought to be barriers that prevent movement of the electrons generated inside of the photoelectric conversion unit 20. Here, the first barrier and the second barrier are Schottky barriers formed at the interfaces between layers. Also, the third barrier is a restriction caused by the reaction speed of a redox reaction.

Also, if the light to be converted is light in a wavelength region on the short wavelength side with respect to the plasmon resonance wavelength, at which localized surface plasmon resonance does not occur in the active layer 40, the amount of electrons generated inside of the photoelectric conversion unit 20 is small. For this reason, it is thought that the electrons inside of the intermediate layer 50 move toward the first barrier (i.e., toward the active layer 40), which is lower than the second bather, in accordance with the height relationship between the first bather and the second barrier, and as a result, a negative photocurrent flows. As the wavelength of the light to be converted increases (i.e., as the plasmon resonance wavelength is approached from the short wavelength side), the amount of electrons generated inside of the photoelectric conversion unit 20 due to the generation of localized surface plasmon resonance and the like increases, but the amount of electrons that can cause the redox reaction is restricted by the third bather. Then, it is thought that the electrons that cannot cause the redox reaction move from the active layer 40 to the intermediate layer 50 and move past the second barrier to the reflection layer 60. That is, if the amount of electrons generated inside of the photoelectric conversion unit 20 increases, the electrons start to move to the side of generating a positive photocurrent. Also, it is thought that if the wavelength of the light to be converted is the specific wavelength, which is shorter than the plasmon resonance wavelength, balance will be achieved between the movement of electrons to the side of generating a negative photocurrent and the movement of electrons to the side of generating a positive photocurrent, and the generated photocurrent approaches zero. It is thought that if the wavelength of the light to be converted is on the long wavelength side with respect to the specific wavelength, many electrons will be generated due to localized surface plasmon resonance in the active layer 40 such that movement of the electrons to the side on which the positive photocurrent is generated takes priority, and as a result, a positive photocurrent flows. Also, it is thought that if the wavelength of the light to be converted is on the long wavelength side with respect to a wavelength near the plasmon resonance wavelength, many electrons are generated inside of the photoelectric conversion unit 20 due to scattered light generated by Mie scattering by the plasmonic particles included in the active layer 40, and in this case as well, a positive photocurrent flows due to the restriction performed by the third barrier.

Also, it is thought that if a bias voltage is applied to the photoelectric conversion unit 20, the height relationship between the above-described barriers changes, whereby the wavelength (i.e., the specific wavelength) at which balance is achieved between the movement of electrons to the side of generating a negative photocurrent and the movement of electrons to the side of generating a positive photocurrent also changes. The measurement results shown in FIG. 18 can be said to be evidence that the specific wavelength changes according to the change in the height relationship between the barriers. Note that by changing the acidity of the electrolytic solution, the height of the third barrier (degree of restriction on the redox reaction) can be changed and thus the specific wavelength can be changed, although the details thereof are omitted.

4. Other Embodiments

Other embodiments of a photoelectric conversion element and a wavelength sensor will be described. Note that the configurations disclosed in the following embodiments can be applied in combination with configurations disclosed in other embodiments, as long as no discrepancy occurs.

(1) The above-described embodiment described an example of a configuration in which the active layer 40 has a structure (stacked body) in which the plasmonic layers 40a and the non-plasmonic layers 40b are stacked alternatingly. However, there is no limitation to this kind of configuration, and it is also possible to use a configuration in which the active layer 40 includes only a single plasmonic layer 40a.

(2) The above-described embodiment described a configuration in which the bottom layer (layer closest to the side from which the light to be converted is emitted) of the stacked body constituting the active layer 40 is a plasmonic layer 40a and the top layer (layer closest to the side on which the light to be converted is incident) of the stacked body constituting the active layer 40 is a plasmonic layer 40a. However, there is no limitation to this kind of configuration, and it is also possible to use a configuration in which one or both of the bottom layer and the top layer of the stacked body constituting the active layer 40 are non-plasmonic layers 40b.

(3) The above-described embodiment described an example of a configuration in which a thin film deposited through the plasmonic material depositing step is made into particles through annealing processing and the plasmonic layers 40a are changed into layers including multiple plasmonic particles. However, there is no limitation to this kind of configuration, and it is also possible to use a configuration in which plasmonic layers 40a including multiple plasmonic particles are formed through a microscopic machining technique, or a configuration in which the plasmonic layers 40a are formed by aligning colloidal plasmonic particles.

(4) The above-described embodiment described an example of a configuration in which the plasmonic layer 40a is a layer including multiple plasmonic particles. However, there is no limitation to this kind of configuration, and for example, it is also possible to use a configuration in which the plasmonic layer 40a is a thin film layer produced using a plasmonic material.

(5) The above-described embodiment described an example of a configuration in which a reflection layer forming step (step #01), an intermediate layer forming step (step #02), and an active layer forming step (step #03) are executed in the stated order as shown in FIG. 2, whereby the photoelectric conversion unit 20 is manufactured. However, there is no limitation to this kind of configuration, and it is also possible to use a configuration in which a photoelectric conversion unit 20 in which an active layer 40, an intermediate layer 50, and a reflection layer 60 are stacked in the stated order starting from the support substrate side is manufactured due to the active layer forming step, the intermediate layer forming step, and the reflection layer forming step being executed in the stated order. In this case, a substrate having transparency with respect to the light to be converted is used as the support substrate, for example.

(6) Regarding other configurations, it is to be understood that the embodiments disclosed in the present specification are in all respects merely exemplary. Accordingly, a person skilled in the art can perform various modifications as appropriate without departing from the gist of the present disclosure.

5. Summary of the Above-Described Embodiment

Hereinafter, an overview of the photoelectric conversion element and the wavelength sensor described above will be described.

A photoelectric conversion element (10) includes a photoelectric conversion unit (20) and electrodes (30) for connecting the photoelectric conversion unit (20) to an external circuit, the photoelectric conversion unit (20) includes an active layer (40) on which light to be converted, which is light that is to be subjected to photoelectric conversion, is incident, an intermediate layer (50) that is arranged on the active layer (40) on a side opposite to the side on which the light to be converted is incident, and a reflection layer (60) that is arranged so as to oppose the active layer (40) with the intermediate layer (50) interposed therebetween, the active layer (40) includes a plasmonic material, which is a material in which plasmonic resonance occurs due to a reciprocal action with the light to be converted, the intermediate layer (50) has both a semiconductor property and transparency with respect to the light to be converted, and the reflection layer (60) has reflectivity with respect to the light to be converted.

According to this configuration, the reflection layer (60), which has reflectivity with respect to the light to be converted, is included on the side (i.e., the side from which the light to be converted is emitted) opposite to the side on which the light to be converted is incident with respect to the active layer (40), and the intermediate layer (50) arranged between the active layer (40) and the reflection layer (60) has transparency with respect to the light to be converted. Accordingly, the light to be converted that has passed through the active layer (40) can be caused to be incident on the active layer (40) once again by being reflected by the reflection layer (60), and the reciprocal action between the light to be converted and the plasmonic material included in the active layer (40) can be strengthened accordingly. In other words, according to the above-described configuration, in comparison with a case in which the intermediate layer (50) and the reflection layer (60) are not included, the reciprocal action between the light to be converted and the plasmonic material included in the active layer (40) can be strengthened, and as a result, the percentage of the light to be converted that is absorbed in the active layer (40) can be increased. Note that the intermediate layer (50) has a semiconductor property in addition to transparency with respect to the light to be converted, and therefore even if such an intermediate layer (50) is provided, movement of the electrons between the active layer (40) and the reflection layer (60) during generation of electrical energy is allowed.

Also, as a result of being able to increase the percentage of the light to be converted that is absorbed by the active layer (40) as described above, it is possible to set the movement directions of electrons between the active layer (40) and the intermediate layer (50) to be opposite to each other in the case where the wavelength of the light to be converted is longer than a specific wavelength and in the case where the wavelength of the light to be converted is shorter than a specific wavelength. Here, the "specific wavelength" is a wavelength that is shorter than the plasmon resonance wavelength. In other words, one electrical phenomenon among an electrical phenomenon in which the electrons move from the active layer (40) to the intermediate layer (50) and an electrical phenomenon in which the electrons move from the intermediate layer (50) to the active layer (40) occurs when the wavelength of the light to be converted is longer than the specific wavelength, and the other electrical phenomenon can be caused to occur when the wavelength of the light to be converted is shorter than the specific wavelength.

As described above, with the above-described configuration, it is possible to realize a photoelectric conversion element (10) in which the movement direction of the electrons in the element changes according to the wavelength of the light to be converted.

Here, it is preferable that the active layer (40) has a configuration in which plasmonic layers (40a) formed using the plasmonic material and non-plasmonic layers (40b) formed using a material that is different from the plasmonic material are stacked alternatingly.

According to this configuration, unlike the case where the active layer (40) has only a single plasmonic layer (40a), the bonding effect of the surface plasmons between the different plasmonic layers (40a) can be used to achieve an increase in the reciprocal action between the light to be converted and the plasmonic material included in the active layer (40).

Also, it is preferable that the plasmonic material is gold, the intermediate layer (50) is formed using titanium oxide, and the reflection layer (60) is formed using gold.

According to this configuration, a photoelectric conversion element (10) in which the light to be converted is light in the visible region can be suitably formed. Also, since the plasmonic material and the material forming the reflection layer (60) are the same material, it is possible to achieve simplicity in the step of manufacturing the photoelectric conversion element (10) compared to the case where the materials are different.

The wavelength sensor (1) includes the photoelectric conversion element (10) and a wavelength information output unit (2) that is electrically connected to the photoelectric conversion element (10), and with a specific wavelength serving as a boundary wavelength, the wavelength information output unit (2) outputs mutually different signals in a case where the wavelength of the light to be converted is longer than the boundary wavelength and in a case where the wavelength of the light to be converted is shorter than the boundary wavelength, the specific wavelength being shorter than a resonance wavelength for plasmon resonance that occurs in the active layer (40).

According to this configuration, it is possible to realize a wavelength sensor (1) that can determine based on the output signal of the wavelength information output unit (2) whether the wavelength of the light to be converted is longer than or shorter than the boundary wavelength. Here, as described above, the movement directions of the electrons between the active layer (40) and the intermediate layer (50) are mutually opposite in the case where the wavelength of the light to be converted is longer than the specific wavelength and in the case where the wavelength of the light to be converted is shorter than the specific wavelength. That is, the directions of the photocurrents generated by the photoelectric conversion element (10) are mutually opposite in the case where the wavelength of the light to be converted is longer than the specific wavelength and in the case where the wavelength of the light to be converted is shorter than the specific wavelength. For this reason, by using the specific wavelength as the boundary wavelength, the magnitude relationship between the wavelength of the light to be converted and the boundary wavelength can be caused to uniformly correspond with the direction of the photocurrent. Also, it is possible to detect the direction of the photocurrent using a configuration that is generally simpler compared to that used in detecting the magnitude of the photocurrent or the like. Accordingly, the wavelength sensor (1) has a configuration according to which it is easy to achieve simplicity in the configuration of the wavelength information output unit (2).

Description of Reference Signs

1 Wavelength sensor
2 Wavelength information output unit

10 Photoelectric conversion element
20 Photoelectric conversion unit
30 Electrode
40 Active layer
40a Plasmonic layer
40b Non-plasmonic layer
50 Intermediate layer
60 Reflection layer

The invention claimed is:

1. A photoelectric conversion element comprising:
a photoelectric conversion unit; and
an electrode for connecting the photoelectric conversion unit to an external circuit,
wherein the photoelectric conversion unit includes an active layer on which light to be converted, which is light that is to be subjected to photoelectric conversion, is incident, an intermediate layer that is arranged on the active layer on a first side opposite to a second side on which the light to be converted is incident, and a reflection layer that is arranged so as to oppose the active layer with the intermediate layer interposed therebetween,
the active layer includes a plasmonic material, which is a material in which plasmon resonance occurs due to a reciprocal action with the light to be converted,
the intermediate layer has both a semiconductor property and transparency with respect to the light to be converted, and
the reflection layer has reflectivity with respect to the light to be converted.

2. The photoelectric conversion element according to claim 1, wherein the active layer has a structure in which plasmonic layers formed using the plasmonic material and non-plasmonic layers formed using a material that is different from the plasmonic material are stacked alternatingly.

3. The photoelectric conversion element according to claim 1, wherein
the plasmonic material is gold,
the intermediate layer is formed using titanium oxide, and
the reflection layer is formed using gold.

4. A wavelength sensor, comprising:
the photoelectric conversion element according to claim 1; and
a wavelength information output unit that is electrically connected to the photoelectric conversion element,
wherein with a specific wavelength serving as a boundary wavelength, the wavelength information output unit outputs mutually different signals in a case where the wavelength of the light to be converted is longer than the boundary wavelength and in a case where the wavelength of the light to be converted is shorter than the boundary wavelength, the specific wavelength being shorter than a resonance wavelength for plasmon resonance that occurs in the active layer.

5. The photoelectric conversion element according to claim 2, wherein
the plasmonic material is gold,
the intermediate layer is formed using titanium oxide, and
the reflection layer is formed using gold.

6. A wavelength sensor, comprising:
the photoelectric conversion element according to claim 2; and
a wavelength information output unit that is electrically connected to the photoelectric conversion element,
wherein with a specific wavelength serving as a boundary wavelength, the wavelength information output unit outputs mutually different signals in a case where the wavelength of the light to be converted is longer than the boundary wavelength and in a case where the wavelength of the light to be converted is shorter than the boundary wavelength, the specific wavelength being shorter than a resonance wavelength for plasmon resonance that occurs in the active layer.

7. A wavelength sensor, comprising:
the photoelectric conversion element according to claim 3; and
a wavelength information output unit that is electrically connected to the photoelectric conversion element,
wherein with a specific wavelength serving as a boundary wavelength, the wavelength information output unit outputs mutually different signals in a case where the wavelength of the light to be converted is longer than the boundary wavelength and in a case where the wavelength of the light to be converted is shorter than the boundary wavelength, the specific wavelength being shorter than a resonance wavelength for plasmon resonance that occurs in the active layer.

* * * * *